United States Patent [19]

Kumagai et al.

[11] Patent Number: 5,777,244
[45] Date of Patent: Jul. 7, 1998

[54] METHOD FOR INSPECTING THE OUTER APPEARANCE OF A GOLF BALL AND ILLUMINATING MEANS USED THEREFOR

[75] Inventors: Hiroki Kumagai; Fumio Fukazawa, both of Chichibu, Japan

[73] Assignee: Bridgestone Sports Co., Ltd., Tokyo, Japan

[21] Appl. No.: 705,261

[22] Filed: Aug. 29, 1996

[30] Foreign Application Priority Data

Aug. 29, 1995 [JP] Japan ................. 7-243684

[51] Int. Cl.⁶ .................................................. B07C 5/02
[52] U.S. Cl. ................................................... 73/865.8
[58] Field of Search .......................... 73/12.02, 865.8, 73/865.9, 104; 348/61, 86, 92, 93, 91, 125, 128; 209/587

[56] References Cited

U.S. PATENT DOCUMENTS

| | | |
|---|---|---|
| 4,726,898 | 2/1988 | Mills et al. ................. 209/587 |
| 5,118,194 | 6/1992 | Mather et al. . |
| 5,166,985 | 11/1992 | Takagi et al. ................. 348/128 |
| 5,187,611 | 2/1993 | White et al. ................. 348/86 |
| 5,585,616 | 12/1996 | Roxby et al. . |

*Primary Examiner*—Robert Raevis
*Attorney, Agent, or Firm*—Sughrue, Mion, Zinn, Macpeak & Seas, PLLC

[57] ABSTRACT

A portion of the surface of a golf ball (g) to be inspected is photographed while uniformly illuminating it with light without any optical disturbances. The golf ball (g) surface is illuminated with diffuse reflection light obtained by reflecting light by a white diffuse reflecting plate (1) having fine irregularities on a surface and/or diffuse transmission light obtained by transmitting light by a white diffuse transmitting plate (4) having fine irregularities on a surface. Using the resulting clear image, the golf ball is inspected for outer appearance.

6 Claims, 4 Drawing Sheets

METHOD FOR INSPECTING THE OUTER APPEARANCE OF A GOLF BALL AND ILLUMINATING MEANS USED THEREFOR

BACKGROUND OF THE INVENTION

1. Field of the Invention

This invention relates to a method for inspecting the outer appearance of a golf ball by operating a camera to take a picture of the golf ball surface to produce a two-dimensional image and detecting any flaw or partial deformation on the ball surface from the two-dimensional image. It also relates to an illuminating apparatus for use in the inspecting method.

2. Prior Art

In the manufacture of golf balls, defects such as flaws and partial deformation can be formed on the golf ball surface. Such defects, even if they are small, can alter the design of dimples formed in the ball surface, thereby affecting the aerodynamics of the ball. It is common practice to carry out outer appearance inspection on golf balls for picking up defective balls prior to shipping.

It has long been desired to incorporate an inspection apparatus in the manufacturing line to automate outer appearance inspection for detecting defects such as flaws and partial deformation. Automatic outer appearance inspection is difficult with golf balls because of their special topography. The present status of outer appearance inspection is by visual observation by workers.

As a substitute for visual inspection, it is commonly employed to automatically inspect the outer appearance of various articles by taking an optical image of an object to be inspected by optical imager means such as a camera, and judging from the image whether or not the outer appearance is acceptable by an image processing means. For high precision inspection, it is essential to evenly illuminate the object with light from an illuminating apparatus to produce a clear image. Where the object to be inspected is a spherical article, however, it is difficult for a single light source to evenly illuminate the spherical surface over its entirety because the angle of illuminating light to the spherical surface largely varies with a position. In the case of golf balls, the surface is not uniform due to the presence of a plurality of dimples. In other words, the golf ball is a spherical body having a lustrous surface of specific and complex topography. When light is illuminated to the golf ball from the illuminating apparatus, there occurs a multiplicity of optical disturbances. It is then very difficult to produce an image having a definite difference between the normal golf ball surface and defects such as flaws and deformation.

This is further discussed with reference to FIG. 5. When a surface of a golf ball is illuminated with light 13 from a single light source located above the golf ball, the light 13 reaches the golf ball surface in a divergent manner. Since the golf ball is a spherical body, light illuminates the surface substantially perpendicularly at its apex (a surface portion nearest to the light source) to provide a maximum illuminance. Apart from the apex, light obliquely illuminates the golf ball surface to provide a lower illuminance. Consequently, the surface of an object to be inspected is not uniformly illuminated with light. Since the excessive illuminance spot "glares," no clear image is available. In this regard, it may be contemplated to adjust the relation between the illuminating angle of light and the shooting angle of a camera so that the reflected light may not directly enter the camera, thereby preventing the occurrence of "glare." In the case of a golf ball having a plurality of dimples formed in its surface, since there are an indefinite plurality of reflecting surfaces attributable to the dimples, the position where "glare" occurs can not be specified. Although a dimple 14a at the apex of the golf ball surface where light 13 reaches substantially at right angles is illuminated with light over its entire area, a land 15 forms a shadow 16 in each of dimples 14b and 14c spaced apart from the apex where light 13 reaches obliquely. The term "land" is the golf ball surface where no dimples are formed. As mentioned above, when a golf ball is illuminated with light, there occur optical disturbances such as "glare" and shadows 16. It is then very difficult to produce an image having a definite difference between such optical disturbances and physical defects (e.g., flaws and partial deformation) on the surface.

For this reason, the state-of-the-art outer appearance inspection of golf balls relies on visual observation by workers as mentioned above. The inspection by visual observation imposes a heavy burden on workers. To visually find a slight deformation or flaw on a golf ball having a plurality of dimples in its surface is a very difficult operation. Upon inspecting golf balls by visual observation, workers frequently overlook flaws and deformation.

SUMMARY OF THE INVENTION

An object of the present invention is to provide a method for inspecting the outer appearance of a golf ball which can uniformly illuminate the golf ball surface with light without optical disturbances while photographing the golf ball surface so that the resulting image is clear enough to detect any flaw or partial deformation on the ball surface.

Another object of the present invention is to provide an illuminating apparatus for use in the inspecting method.

In connection with a process of photographing a golf ball under illumination, we have found that an objective area of the golf ball surface can be evenly illuminated with light without giving rise to "glare" and shadow by illuminating the golf ball with reflected light or indirect light transmitted by a filter rather than irradiating light directly from a light source to the golf ball surface. The indirect light used herein is diffuse reflection light obtained by reflecting light by a white diffuse reflecting plate having fine irregularities on a surface or diffuse transmission light obtained by transmitting light by a white diffuse transmitting plate having fine irregularities on a surface. There is obtained a clear image which allows for definite judgment of flaws and partial deformation on the golf ball surface. Consequently, golf balls can be inspected for outer appearance in an effective and reliable manner.

According to a first aspect of the invention, there is provided a method for inspecting the outer appearance of a golf ball, comprising the steps of operating a camera to take a picture of the surface of a golf ball to produce a two-dimensional image while illuminating light to the ball surface, and detecting any flaw or deformation on the ball surface from the two-dimensional image. The light used for illumination is diffuse reflection light obtained by reflecting light by a white diffuse reflecting plate having fine irregularities on a surface or diffuse transmission light obtained by transmitting light by a white diffuse transmitting plate having fine irregularities on a surface or both.

The inventors also made a study on the illuminating apparatus suitable for use in the inspection method according to the invention. A housing is formed of a white diffuse reflecting plate having fine irregularities on a surface, the golf ball is placed in the housing, and a light source is disposed in the housing, whereby light from the light source is reflected and diffused by the inner surface of the housing into diffuse reflection light with which the golf ball is illuminated. When a white diffuse transmitting plate having fine irregularities on a surface is interposed between the golf ball and the light source, light from the light source is transmitted by the diffuse plate into diffuse transmission light with which the golf ball is also illuminated. Then the ball is evenly illuminated. Alternatively, when a housing is formed of a white diffuse transmitting plate having fine irregularities on a surface, the golf ball is placed in the housing, and a light source is disposed outside the housing, light from the light source is transmitted by the housing into diffuse transmission light with which the golf ball is illuminated. Then the ball is evenly illuminated.

According to a second aspect of the invention, there is provided an illuminating apparatus for use in inspecting the outer appearance of a golf ball, comprising a housing having a bottom and a peripheral wall defining a space therein for receiving the ball, the peripheral wall being formed of a white diffuse reflecting plate having fine irregularities on a surface; a light source disposed in the housing at its bottom; a support on the housing bottom spaced from said light source for supporting the ball at an upper end; a white diffuse transmitting plate having fine irregularities on a surface interposed between said light source and the upper end of said support; and at least one opening in the peripheral wall of said housing through which the ball is viewed for photographing. The golf ball is supported at the upper end of said support and the light source is operated to emit light which is not only reflected by the peripheral wall of the housing into diffuse reflection light, but also transmitted by the diffuse transmitting plate into diffuse transmission light so that the golf ball surface is illuminated with the diffuse reflection light and the diffuse transmission light, while the golf ball is photographed from outside the housing through said opening for performing inspection of the outer appearance of the golf ball.

The present invention further provides an illuminating apparatus for use in inspecting the outer appearance of a golf ball, comprising a housing having a peripheral wall defining a space therein for receiving the ball, the peripheral wall being formed of a white diffuse transmitting plate having fine irregularities on a surface; a light source disposed outside the housing; means in the housing for supporting the ball; and at least one opening in the peripheral wall of said housing through which the ball is viewed for photographing. The golf ball is supported by said support means and the light source is operated to emit light which is transmitted by the peripheral wall of the housing formed of diffuse transmitting plate into diffuse transmission light so that the golf ball surface is illuminated with the diffuse transmission light, while the golf ball is photographed from outside the housing through said opening for performing inspection of the outer appearance of the golf ball.

BRIEF DESCRIPTION OF THE DRAWINGS

These and further features of the present invention will be apparent with reference to the following description and drawings, wherein.

DETAILED DESCRIPTION OF THE INVENTION

In the method for inspecting the outer appearance of a golf ball according to the invention, when the golf ball surface is photographed to produce a two-dimensional image, the golf ball surface is illuminated with diffuse reflection light obtained by reflecting light by a white diffuse plate having fine irregularities on a surface or diffuse transmission light obtained by transmitting light by a similar diffuse plate or both. More particularly, the golf ball is photographed while illuminating it with an apparatus as shown in FIG. 1.

Figure 1:
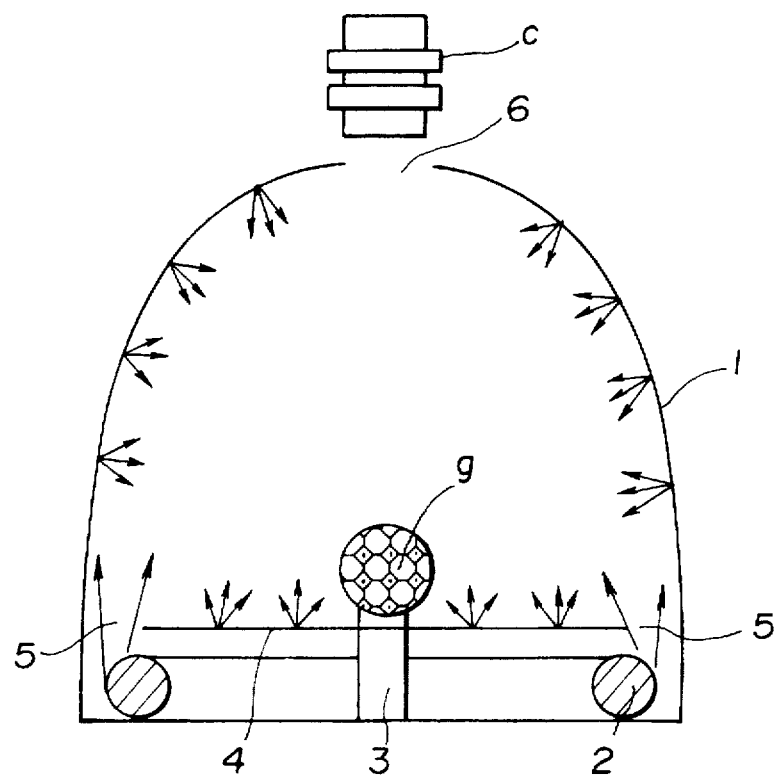
FIG. 1 is a schematic view of an outer appearance inspecting method and an illuminating apparatus according to one embodiment of the invention.

FIG. 1 illustrates one exemplary illuminating apparatus for use in carrying out the outer appearance inspecting method according to the invention. The apparatus includes a hollow dome-shaped housing 1 having a bottom and a peripheral wall defining a space therein for receiving a golf ball g therein. The housing peripheral wall is formed of a white diffuse reflecting plate having fine irregularities on a surface. An annular light source 2 is disposed in the housing 1 on its bottom. An upright pole or support 3 for supporting the ball g at its upper end is secured on the housing bottom at the center of the annular light source 2. The support 3 extends upright above the light source 2. A white diffuse transmitting plate 4 having fine irregularities on a surface is held by the support 3 slightly below its upper end such that the plate 4 extends parallel to the bottom of the housing 1. Differently stated, the diffuse transmitting plate 4 is interposed between the light source 2 and the upper end of the support 3. More particularly, the diffuse transmitting plate 4 is a disc having a smaller diameter than the inner diameter of the peripheral wall of the housing 1 near its bottom so that a gap 5 is left between the peripheral edge of the diffuse transmitting plate 4 and the inner surface of the housing 1. An opening 6 is perforated in the peripheral wall of the housing 1 at the top through which the ball g is viewed for a camera c to photograph the ball.

When the golf ball g is inspected for outer appearance using this illuminating apparatus, the golf ball g is supported at the upper end of the support 3 and the light source 2 is operated to emit light. While the golf ball g is illuminated with light, it is photographed by the camera c through the opening 6 to produce a two-dimensional image. Flaws and partial deformation on the surface of the golf ball g are detected from the two-dimensional image.

A portion of light emitted from the light source 2 which passes through the gap 5 is reflected and diffused by the peripheral wall of the housing 1, that is, the inner surface of the diffuse reflecting plate into diffuse reflection light. The diffuse reflection light is further reflected and diffused by the inner surface of the housing 1 and the diffuse transmitting disc 4. The space within the housing 1 is evenly illuminated with diffuse reflection light. Another portion of light emitted from the light source 2 which directly reaches the diffuse transmitting disc 4 is transmitted by the diffuse transmitting disc 4 into diffuse transmission light which also disperses in the housing 1.

Figure 2:
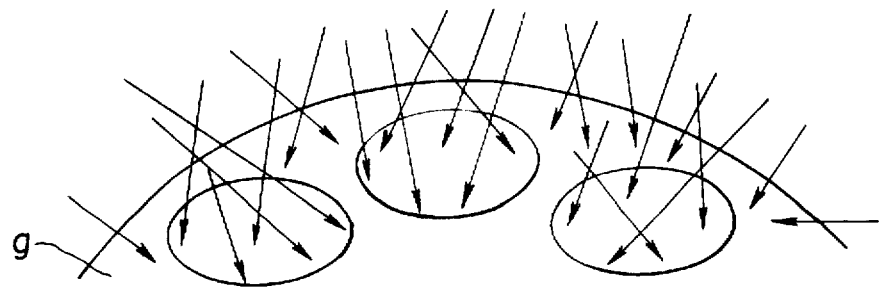
FIG. 2 illustrates how a golf ball surface is illuminated when the outer appearance inspecting method and the illuminating apparatus according to the invention are used.

Then the golf ball g received in the housing 1 is not illuminated with direct light from the light source 2, but with diffuse reflection light and diffuse transmission light in all directions. No optical disturbances such as glare and shadows occur on the surface of the golf ball g. As illustrated in FIG. 2, the surface of the golf ball g is evenly illuminated with diffuse reflection light and diffuse transmission light in all directions without a local change of illuminance over the surface. A portion of the surface of the golf ball g to be inspected (or a portion to be photographed by the camera c) is thus illuminated to an equal illuminance, causing no "glare" on the surface of the golf ball g. Since the golf ball g is evenly illuminated at any position with diffuse reflection light and diffuse transmission light from all directions, dimples are evenly illuminated on their concave surface independent of their location and no shadow is formed over the surface of the golf ball g.

When the golf ball g is photographed under illumination by the illuminating apparatus mentioned above, a clear image is captured because the illuminating apparatus causes no optical disturbances such as "glare" and shadow and light from the light source 2 does not directly enter the camera c which is located outside the housing 1. The clear image allows flaws and partial deformation formed on the surface of the golf ball g to be detected with ease, ensuring high precision inspection of outer appearance. This outer appearance inspection can be automated if the image is processed by suitable means for automatically detecting defects such as flaws and partial deformation.

The diffuse reflecting plate of which the housing 1 is formed is a white plate having fine irregularities on a surface so that incident light may be effectively reflected and diffused thereby. Examples include paper and fabric having a white surface and a plate having a ragged surface which is coated with a white coating.

The diffuse transmitting plate 4 is a white plate having fine irregularities on a surface so that incident light may be effectively transmitted and diffused thereby. Examples include paper and fabric having a white surface and a plate having a ragged surface which is coated with a white coating as long as they are light transmissive.

It is understood that although the use of the diffuse transmitting plate 4 in the illuminating apparatus of FIG. 1 is preferable in that the golf ball g is given uniform diffuse light, a diffuse reflecting plate which is not light transmissive may be similarly disposed instead of the diffuse transmitting plate 4. In this case, an inward portion of light from the light source 2 is shut out by the diffuse reflecting plate so that light does not directly reach the golf ball g. Alternatively, merely a shielding plate rather than the diffuse plate may be used so that no light may directly reach the golf ball g.

The light source 2 used herein is preferably a conventional circular fluorescent lamp. Although the use of an annular light source is preferred in that the golf ball g is given uniform diffuse light as seen from FIG. 1, it is acceptable to use a single bulbous light source or to arrange a plurality of bulbous light sources at an equal spacing.

Figure 3A:
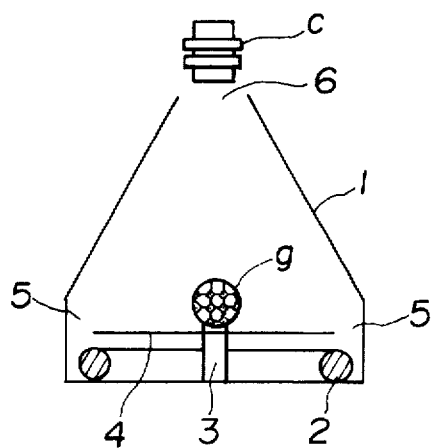
FIGS. 3A to 3F are schematic views showing variants of the outer appearance inspecting method and the illuminating apparatus according to the invention.
Figure 3B:
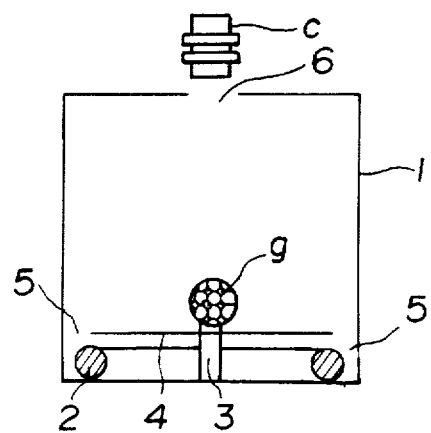
Figure 3C:
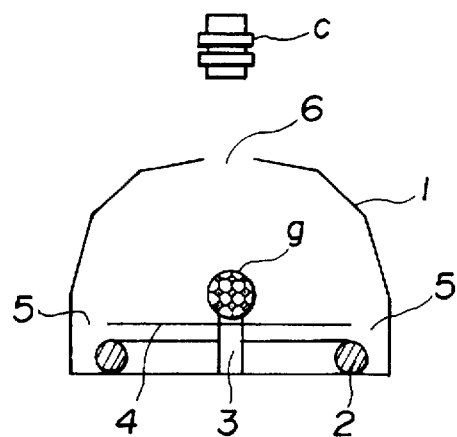
Figure 3D:
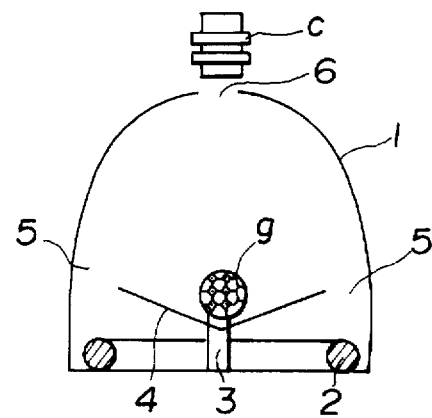
Figure 3E:
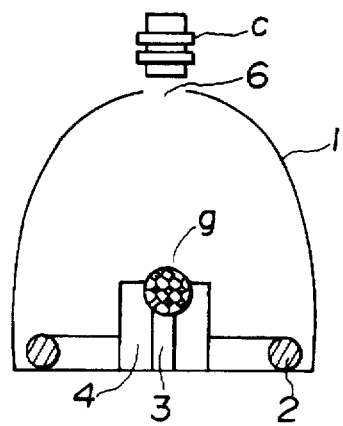

It is understood that the shape of the housing 1 and diffuse transmitting plate 4 can be changed as desired. Variants are shown in FIG. 3. The ball-accommodating housing 1 may be formed to a flask shape as shown in FIG. 3A, a rectangular box shape as shown in FIG. 3B or a polyhedral dome shape as shown in FIG. 3C. The diffuse transmitting plate 4 may be formed to a funnel shape as shown in FIG. 3D or a cylindrical shape which circumscribes the golf ball g as shown in FIG. 3E.

Figure 3F:
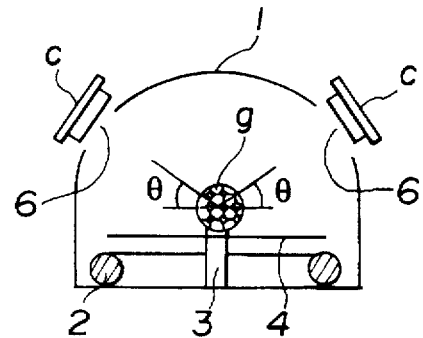

Another embodiment is shown in FIG. 3F wherein a plurality of, two in the figure, cameras c are used to take pictures of a corresponding plurality of areas of the surface of the golf ball g to be inspected. This makes the outer appearance inspection more efficient. Since any objective area of the golf ball surface is uniformly illuminated with the illuminating apparatus according to the invention, a clear image can be taken by every camera c without a need for adjusting the light source 2. Satisfactory outer appearance inspection can be carried out in an effective manner. In the apparatus of FIG. 3F using two cameras c and c, it is preferred to orient the cameras at a shooting angle θ of 30° with respect to a horizontal line.

Figure 4A:
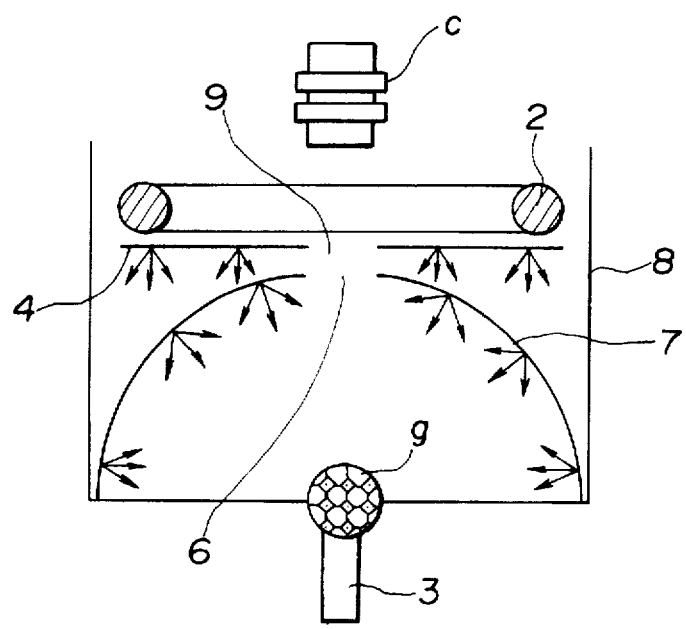
FIG. 4A is a schematic view of an outer appearance inspecting method and an illuminating apparatus according to another embodiment of the invention.

FIG. 4A illustrates another exemplary illuminating apparatus for use in carrying out the outer appearance inspecting method according to the invention. This illuminating apparatus includes a housing 7 having a bottom and a hemispherical wall defining a space therein for receiving a golf ball g. The hemispherical wall is formed of a white diffuse transmitting plate having fine irregularities on its inner surface. An annular light source 2 is disposed outside and above the housing 7. A diffuse transmitting disc 4 as used in the apparatus of FIG. 1 is disposed between the light source 2 and the housing 7. Preferably the annular light source and transmitting disc 4 are parallel to the bottom of the housing 1. Ball support means is in the form of an upright support 3 which is disposed outside the housing 7 for supporting the golf ball g such that an upper hemispherical portion of the ball g is exposed in the housing 7 and above its bottom. A cylindrical enclosure 8 circumscribes the housing 7, diffuse transmitting disc 4, and light source 2. An opening 6 is perforated in the hemispherical wall of the housing 7 at its top through which the ball is viewed for photographing. The diffuse transmitting disc 4 is also provided with a central opening 9. The golf ball g received in the housing 7 can be photographed by a camera c through the openings 6 and 9.

When the golf ball g is illuminated with the illuminating apparatus mentioned above, light from the light source 2 is transmitted by the diffuse transmitting disc 4 into diffuse transmission light which reaches the housing 7 and is transmitted thereby into further diffused transmission light with which the interior of the housing 7 is uniformly illuminated. Then an objective portion of the surface of the golf ball g to be inspected is illuminated with diffuse light from all directions so that a clear image without glare or shadow is obtained.

In the illuminating apparatus of FIG. 4A, light is emitted from the light source 2 disposed outside the housing 7 and transmitted by the diffuse transmitting plate of which the housing 7 is made, obtaining diffuse transmission light with which the golf ball g is illuminated. The diffuse transmitting plate from which the housing 7 is made may be selected from paper and fabric having a white surface and a plate having a ragged surface which is coated with a white coating as in the apparatus of FIG. 1, as long as they are light transmissive so that incident light is transmitted thereby to change into diffused and transmitted light.

It is preferred to provide the diffuse transmitting disc 4 in the apparatus of FIG. 4A in order to prevent light from the light source 2 from directly entering the interior space of the housing 7 through the opening 6 although the disc 4 can be omitted in some cases. The enclosure 8 is preferably made of a diffuse reflecting plate so that diffuse light is reflected thereby although the enclosure 8 may be merely a shielding plate. The enclosure 8 itself can be omitted in some cases. In the embodiment of FIG. 4A wherein light from the light source 2 reaches the housing 7 after it is transmitted by the diffuse transmitting disc 4 and changed into diffused and transmitted light, the housing 7 need not necessarily be made of a plate having fine irregularities on a surface.

Figure 4B:
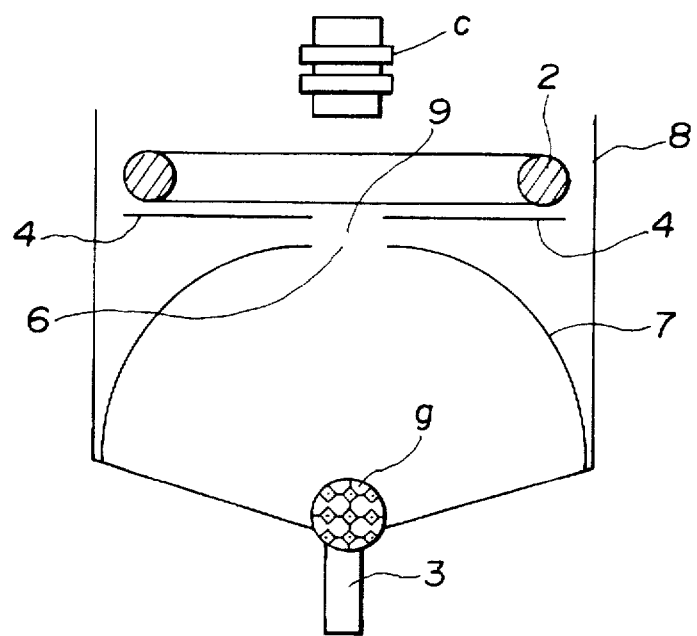
FIG. 4B is a schematic view of a variant of the embodiment of FIG. 4A.
Figure 5:
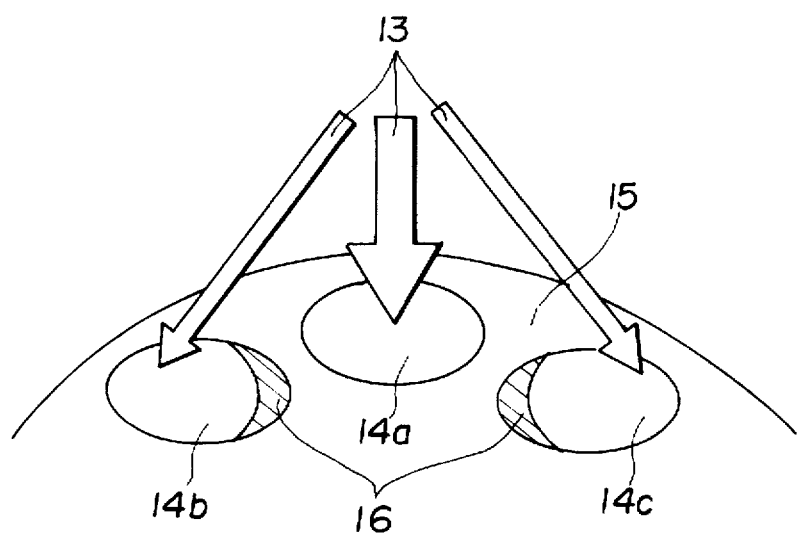
FIG. 5 illustrates how a golf ball surface is illuminated when the prior art outer appearance inspecting method and illuminating apparatus are used.

The remaining components and benefits are the same as in the illuminating apparatus of FIG. 1. The shape of the housing 7 may also be changed in various ways as in the illuminating apparatus of FIG. 1. For example, it is acceptable that the bottom of the housing 7 is formed in a funnel shape and the golf ball g is held at the center thereof as shown in FIG. 4B. The peripheral wall of the housing 7 may take any shape including flask, box, and polyhedral dome shapes as shown in FIGS. 3A to 3C.

The outer appearance inspecting method and illuminating apparatus according to the present invention, a portion of the surface of a golf ball to be inspected can be photographed while uniformly illuminating it with light without any optical disturbances. Since a clear image of the golf ball surface portion is obtained, flaws and partial deformation on the golf ball surface can be detected from the image without errors.

We claim:

1. A method for inspecting the outer appearance of a golf ball, comprising the steps of:

operating a camera to take a picture of the surface of a golf ball to produce a two-dimensional image while illuminating light to the ball surface, and detecting any flaw or deformation on the ball surface from the two-dimensional image, wherein a housing selected from a dome shape, a flask shape, a rectangular box shape and a polyhedral dome shape is formed of a white diffuse reflecting plate having fine irregularities on a surface for receiving the ball therein, a light source is disposed in the housing, and a white diffuse transmitting plate having fine irregularities on a surface is interposed between the golf ball and the light source, said method further comprising the step of operating the light source to emit light which is reflected by the inner surface of the housing into diffuse reflection light, and also transmitted by the diffuse transmitting plate into diffuse transmission light so that the golf ball surface is illuminated with both the diffuse reflection light and the diffuse transmission light, and wherein the golf ball is directly photographed from outside the housing through at least one opening in the peripheral wall of the housing for performing inspection of the outer appearance of the golf ball.

2. The method of claim 1 further comprising the steps of positioning a second camera adjacent a second opening in the peripheral wall of said housing spaced from said at least one opening and, photographing said golf ball with said second camera to perform an inspection of the outer appearance of the golf ball.

3. An illuminating apparatus for use in inspecting the outer appearance of a golf ball, comprising a housing selected from a dome shape, a flask shape, a rectangular box shape and a polyhedral dome shape having a bottom and a peripheral wall defining a space therein for receiving the golf ball, the peripheral wall being formed of a white diffuse reflecting plate having fine irregularities on a surface, a light source disposed in the housing at its bottom, a support on the housing bottom spaced from said light source for supporting the golf ball at an upper end, a white diffuse transmitting plate having fine irregularities on a surface interposed between said light source and the upper end of said support, and at least one opening in the peripheral wall of said housing through which the golf ball is viewed for photographing, wherein the golf ball is supported at the upper end of said support and the light source is operated to emit light which is reflected by the peripheral wall of the housing into diffuse reflection light, and also transmitted by the diffuse transmitting plate into diffuse transmission light so that the golf ball surface is illuminated with both the diffuse reflection light and the diffuse transmission light, whereby the golf ball is directly photographed from outside the housing through said opening for performing inspection of the outer appearance of the golf ball.

4. The illuminating apparatus of claim 3 wherein said light source is annular and the golf ball support is located at the center of the annular light source.

5. An illuminating apparatus for use in inspecting the outer appearance of a golf ball, comprising a housing selected from a dome shape, a flask shape, a rectangular box shape and a polyhedral dome shape having a peripheral wall defining a space therein for receiving the golf ball, the peripheral wall being formed of a white diffuse transmitting plate having fine irregularities on a surface, a light source disposed outside the housing, means for supporting the golf ball in the housing, and at least one opening in the peripheral wall of said housing through which the golf ball is viewed for photographing, wherein the golf ball is supported by said support means and the light source is operated to emit light which is transmitted by the peripheral wall of the housing formed of diffuse transmitting plate into diffuse transmission light so that the golf ball surface is illuminated with the diffuse transmission light, while the golf ball is directly photographed from outside the housing through said opening for performing inspection of the outer appearance of the golf ball, wherein said light source is annular and said opening is located in the peripheral wall of said housing at a position corresponding to the center of the annular light source whereby the golf ball in the housing is photographed through said annular light source and said opening.

6. The illuminating apparatus of claim 5 further comprising a second white diffuse transmitting plate having fine irregularities on a surface disposed between said annular light source and said housing, anal second transmitting plate being formed at the center with an opening for photographing.

* * * * *